United States Patent
Handjani et al.

(10) Patent No.: US 6,203,802 B1
(45) Date of Patent: Mar. 20, 2001

(54) COMPOSITION FOR THE COSMETIC AND/OR PHARMACEUTICAL TREATMENT OF THE UPPER LAYERS OF THE EPIDERMIS BY TOPICAL APPLICATION TO THE SKIN, AND CORRESPONDING PREPARATION PROCESS

(75) Inventors: Rose-Marie Handjani; Alain Ribier, both of Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/195,081

(22) Filed: Feb. 14, 1994

Related U.S. Application Data

(63) Continuation of application No. 07/961,537, filed on Oct. 15, 1992, now abandoned, which is a continuation of application No. 07/668,308, filed on Mar. 13, 1991, now abandoned.

(30) Foreign Application Priority Data

Mar. 16, 1990 (FR) .................................................. 90 03418

(51) Int. Cl.⁷ ................................. A61K 7/48; A61K 9/51
(52) U.S. Cl. ......................... 424/401; 424/489; 424/499; 424/501; 514/951
(58) Field of Search ..................................... 424/401, 489, 424/502, 450, 499, 501; 514/946, 947, 950, 951

(56) References Cited

U.S. PATENT DOCUMENTS

| | | | |
|---|---|---|---|
| 3,516,941 | 6/1970 | Matson | 424/497 |
| 3,965,033 | 6/1976 | Matsukawa et al. | 424/497 |
| 4,329,332 | 5/1982 | Couvreur et al. | 424/501 |
| 4,489,055 * | 12/1984 | Couvreur et al. | 424/1.37 |
| 4,880,617 | 11/1989 | Chromecek | 424/501 |
| 4,897,267 | 1/1990 | Bontemps et al. | 424/489 |
| 4,917,892 | 4/1990 | Speaker et al. | 424/487 |
| 4,976,961 | 12/1990 | Norbury et al. | 424/401 |
| 5,118,528 * | 6/1992 | Fessi et al. | 427/213.36 |
| 5,133,908 * | 7/1992 | Stainmesse et al. | 264/4.1 |
| 5,139,783 | 8/1992 | Handjani et al. | 424/401 |
| 5,919,487 * | 7/1999 | Simonnet et al. | 424/490 |

FOREIGN PATENT DOCUMENTS

| | | |
|---|---|---|
| 47099 * | 6/1990 | (AU) . |
| 0274961 | 7/1988 | (EP) . |
| 0330180 | 8/1989 | (EP) . |
| 2515960 | 5/1983 | (FR) . |

OTHER PUBLICATIONS

French Search Report of FR 90 03418.

* cited by examiner

Primary Examiner—Robert H. Harrison
(74) Attorney, Agent, or Firm—Nixon & Vanderhye P.C.

(57) ABSTRACT

Composition comprising biodegradable nanoparticles encapsulating oils which are active and/or which contain an active ingredient having a cosmetic and/or pharmaceutical action in the upper layers of the epidermis. The nanoparticles are preferably prepared from a polymer of $(C_2$–$C_{12})$ alkyl cyanoacrylate.

11 Claims, No Drawings

COMPOSITION FOR THE COSMETIC AND/ OR PHARMACEUTICAL TREATMENT OF THE UPPER LAYERS OF THE EPIDERMIS BY TOPICAL APPLICATION TO THE SKIN, AND CORRESPONDING PREPARATION PROCESS

This is a continuation of Application No. 07/961,537, filed Oct. 15, 1992, now abandoned which is a Rule 60 continuation of Ser. No. 07/668,308 filed Mar. 13, 1991, now abandoned.

The present invention relates to a composition for the cosmetic and/or pharmaceutical treatment of the upper layers of the epidermis, by topical application of the said composition to the skin, and a preparation process for obtaining it.

It is well known in cosmetics and/or in pharmacy to apply to the skin oils which are active and/or which contain an active ingredient. These oils are used as they are or, more often, in the form of a water-in-oil or oil-in-water emulsion. These oils are known to have an action on the surface of the skin, but also in the upper layers of the epidermis, since they pass through the stratum corneum, the cosmetic and/or pharmaceutical action of the oils generally increasing in efficacy with an increase in the proportion of oil penetrating into the upper layers of the epidermis.

Moreover, nanoparticles are known: this name is used to denote colloidal particles of the order of 10 to 1,000 nm in size consisting of polymeric materials, in which an active principle is trapped, encapsulated and/or adsorbed (see J. KREUTER, J. MICROENCAPSULATION 1988, Vol. 5, pages 115–127). The term nanoparticles can be used to denote nanospheres and nanocapsules: a nanosphere constitutes a porous solid polymer matrix on which the active ingredient is adsorbed; a nanocapsule is a polymer membrane surrounding a core consisting of the active principle. For the remainder of the description and in the claims, the scope of the term "nanoparticles" will be strictly limited to nanocapsules defined above. Among polymers which may be used for the manufacture of nanoparticles, biodegradable materials are preferably selected in order to enable the said nanoparticles to be used therapeutically. It is known that cyanoacrylates, and especially polyalkyl cyanoacrylates, enable biodegradable nanoparticles to be obtained; the preparation of nanoparticles from cyanoacrylates is described in EP-B-0,007,895 and EP-B-0,064,967.

The use of biodegradable nanoparticles encapsulating biologically active compounds has been proposed in many therapeutic applications for many active principles, such as antimitotic or antineoplastic substances, antibiotics, hormonal substances, insulin, heparin or biological products such as proteins, antigens or the constituents of viruses, bacteria or cells. It has hence already been proposed to administer nanoparticles encapsulating active principles orally, subcutaneously, intradermally, intramuscularly, intravenously and by application to the eye (see EP-B-0,007,895, EP-B-0,064,967, FR-B-2,604,903, DE-A-3,722,837, DE-A-3,341,001 and FR-B-2,304,326).

In FR-A-2,515,960, nanoparticles of cyanoacrylate encapsulating an oil or an active substance dispersed in an oil have been described, and it is specified that these nanoparticles can be administered orally, subcutaneously, intradermally, intramuscularly or intravenously. In addition, in this document, the use of nanoparticles for encapsulating perfumes has been described, the encapsulated perfumes having the advantage of causing the perfume odor to persist longer after application than in the case where the perfume is applied to the skin without encapsulation; encapsulation hence has a delay action on the perfume. In addition, in this case, the desired action of the perfume takes place at the surface of the skin, and the persistence of the odor is completely independent of the fate of the fraction of the nanoparticles which might possibly pass through the stratum corneum. This topical application hence provides no information as to the possible capacity of the nanoparticles to pass through the stratum corneum and to be degraded in the upper layers of the epidermis; it leads, on the contrary, to the prediction that the nanoparticles would remain predominantly at the surface of the skin, since they permit release of the perfume.

According to the present application, it was found that, by cutaneous topical application of a composition comprising biodegradable nanoparticles encapsulating oils which are active and/or which contain an active ingredient, an especially effective cosmetic and/or pharmaceutical action was obtained.

The improvement in the cosmetic and/or pharmaceutical efficacy of the oils as a result of encapsulation in nanoparticles could in no way be foreseen; it was not obvious, in effect, on the one hand that the nanoparticles would pass through the stratum corneum more readily than the unencapsulated oil, whether the latter is in the form of a water-in-oil or oil-in-water emulsion, and on the other hand that these nanoparticles would be biodegraded in the upper layers of the epidermis. It was known, admittedly, that the proposed forms for administration in the human body, especially by injection, lead to biodegradation of the nanoparticles in the different tissue regions in which they are introduced. However, it is well known that different tissues have different constitutions and contain different enzymes; in particular, it is well known that the connective tissue of muscle, dermis and the deep layers of the skin, where the nanoparticles had previously been introduced by injection, have a very different biochemical constitution from that of the upper layers of the epidermis (see, for example, British Journal of Dermatology (1976) 94, 443).

Hence, nothing enabled those skilled in the art to anticipate that the nanoparticles were, on the one hand capable of passing through the stratum corneum in significant amounts, and on the other hand capable of releasing the active ingredient very rapidly into the upper layers of the epidermis.

According to the present invention, it was found, in addition, that the encapsulation of an active oil (or one containing an active ingredient) in nanoparticles produced, surprisingly, an immediate action of the composition. The delay effect reported for the perfuming compositions applied topically in the document FR-A-2,515,960 cited above led those skilled in the art to anticipate that a topical application, assuming it to be capable of having an effect, could have only a delayed action. The invention hence proposes a composition whose properties are unexpected. Moreover, these properties are especially well suited to topical administration, as was shown in a comparative in vitro study of percutaneous absorption.

The subject of the present invention is consequently a composition for the cosmetic and/or pharmaceutical treatment of the upper layers of the epidermis, by topical application to the skin, characterised in that it comprises, in a suitable vehicle, biodegradable polymer nanoparticles encapsulating at least one active ingredient in the form of an oil and/or at least one active ingredient contained in an inactive carrier oil or an active oil, the active ingredient being selected from those having a cosmetic and/or pharmaceutical action.

The nanoparticles used are preferably between 10 and 1000 nm, and more especially between 50 and 500 nm, in size.

The weight of the nanoparticles loaded with at least one active ingredient advantageously constitutes from 0.1% to 20% of the total weight of the composition, and preferably from 0.5 to 5%. by weight.

The polymers constituting the biodegradable nanoparticles can be polymers of $C_2$–$C_{12}$, and especially $C_2$–$C_6$, alkyl cyanoacrylate; the alkyl radical is preferably selected from the group composed of ethyl, n-butyl, hexyl, isobutyl and isohexyl radicals. The biodegradable polymers may also be taken from the group composed of poly-L-lactides, poly-DL-lactides, polyglycolides, polycaprolactones, polymers of 3-hydroxybutyric acid and the corresponding copolymers, such as copoly(DL-lactides/glycolides), copoly(glycolides/caprocolatones) and the like.

The use of nanoparticles obtained from poly-L-lactides, poly-DL-lactides and copoly(DL-lactides/glycolides) is especially advantageous, since the products of enzymatic or chemical biodegradation of these nanoparticles can themselves have cosmetic effects: thus, lactic acid exhibits humectant and plasticising properties; and glycolic acid exhibits depigmenting and/or biostimulatory properties.

The active ingredients in the form of an oil (or active oils) are preferably selected from the group composed of α-tocopherol, α-tocopherol acetate, triglycerides rich in linoleic and/or linolenic acid(s), pentaerythritol tetra(2-ethylhexanoate), clofibrate, tocopherol linoleate, fish oil, hazelnut oil, bisabolol, farnesol, farnesyl acetate, ethyl linoleate and ethylhexyl para-methoxycinnamate.

The inactive carrier oils are preferably selected from the group composed of triglycerides, simple or modified, especially by oxyethylenation, volatile silicone oils and mixtures thereof.

To obtain the loaded nanoparticles used in the composition according to the invention it is possible either to take an active oil, or to introduce into an active oil or into a carrier oil which is in itself inactive, any active ingredient capable of having a cosmetic or therapeutic activity. These active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, β-carotene, γ-orizanol and stearyl glycerate.

The active ingredient is preferably an oleophilic active ingredient in the form of a solution in the oil. However, it can also be in the form of a dispersion, suspension or emulsion.

In the nanoparticles, the weight ratio of the biodegradable polymer of the nanoparticles to the active oily phase is preferably between 0.05 and 0.5, and in particular in the region of 0.2.

The compositions according to the invention can take the form of a physiological fluid, a lotion, an aqueous, aqueous-alcoholic or oily gel or a water-in-oil or oil-in-water emulsion, or alternatively of aqueous dispersions of vesicles in which the constituent lipids are ionic or nonionic lipids or a mixture of ionic and nonionic lipids, with or without an oily phase. Their use to constitute physiological fluids is especially advantageous: in effect, this type of product requires the introduction of a large amount of emulsifier in the case where it is desired to introduce unencapsulated oily active ingredients into them, and it is well known that emulsifiers have the effect of irritating the skin and are not compatible with all active ingredients.

The compositions can contain, in addition to the nanoparticles, known cosmetically and/or pharmaceutically acceptable adjuvants, such as fats, vaseline, preservatives, thickening agents, colorings and perfumes.

When a polymer of ($C_2$–$C_{12}$) alkyl cyanoacrylate is used to obtain the nanoparticles of the composition, an interfacial polymerisation of a microemulsion of oil in an aqeuous-alcoholic medium is performed, as described, for example, in FR-A-2,515,960, by injecting, into an aqeuous phase containing or otherwise one surfactant, a mixture consisting of the oil(s) to be encapsulated, at least one ($C_2$–$C_{12}$) alkyl cyanoacrylate and at least one solvent which can contain one surfactant, then evaporating off the solvent and optionally concentrating the aqueous dispersion of nanoparticles obtained. The solvent used is, more often than not, a $C_2$–$C_4$ lower alcohol, especially ethanol, propanol, isopropanol or a mixture of these alcohols, or alternatively acetone; it can optionally contain one surfactant.

It is also possible to use the process for manufacturing nanoparticles described in European Patent Application No. 0,274,961. In this case, the nanoparticles are obtained by precipitation of the polymer around a dispersion of oily droplets, by injecting, into an aqueous phase containing or otherwise one surfactant, a mixture consisting of the oil(s) to be encapsulated, at least one polymer and at least one solvent containing or otherwise one surfactant, and then evaporating off the solvent.

Other processes may also be used.

The surfactant optionally used in the preparation process can consist of at least one nonionic surfactant, more especially selected from the condensates of glycerol, ethylene oxide and propylene oxide, or of at least one ionic surfactant which can, in particular, be taken from the phospholipid group, such as lecithin, or alternatively of a mixture of at least one surfactant of each of these two categories. This surfactant promotes the formation of the microemulsion of oil, and prevents coalescence of the nanoparticles within the reaction mixture. The weight ratio of the surfactant used on the one hand, to the materials constituting the nanoparticles loaded with active ingredient(s) on the other hand, is advantageously between 0.01 and 0.5, and preferably in the region of 0.2.

When a surfactant used during the process for manufacturing the nanoparticles is in itself capable of forming vesicles consisting of lipid lamellae encapsulating a closed space, the said surfactant behaves in a fundamentally different way according to whether it is introduced into the aqeuous phase or into the solvent phase. If the surfactant is in the aqueous phase, it has a tendency, at least partially, to form vesicles. If, on the other hand, the surfactant is in the solvent phase, it has a tendency, at least partially, to form one or more lipid lamellae, each consisting of a molecular bilayer, around the polymer membrane of each nanoparticle.

In the case where the oil to be encapsulated is a self-emulsifying oil, selected, for example, from oxyethylenated triglycerides, it is not necessary to use a surfactant.

The aqueous dispersion of nanoparticles obtained may be used as it is. It can also be lyophilized, in particular in the presence of anticaking additives such as silicas, sugars, salts, proteins, peptides and amino acids. The lyophilizates have the advantage of enabling anhydrous cosmetic compositions to be prepared. If the nanoparticles are coated with at least one lipid lamella consisting of at least one surfactant capable of forming vesicles, the compositions according to the invention can exhibit especially advantageous cosmetic features. These coated nanoparticles can constitute only a part of the nanoparticles of the composition.

The examples given below, purely by way of illustration and without implied limitation, will facilitate understanding of the invention.

EXAMPLE 1

In this example, for the purpose of comparison, an aqeuous dispersion of nanoparticles of polymer of butyl cyanoacrylate containing α-tocopherol, prepared according to the procedure of Example 3, in an aqueous phase containing a surfactant and ethanol, and two emulsions of α-tocopherol in water obtained using two different emulsifiers, were studied. Skin irritation (SIR) and eye irritation (EI) were then measured.

The SIR measurements were performed according to the protocol described in the Ministerial Decree of Feb. 1, 1982, published in the Journal Officiel de la République Française (J.O.R.F) (Official Journal of the French Republic) dated Feb. 21, 1982.

The EI measurements were performed according to the protocol described in the Ministerial Decree of Sep. 21, 1984, published in the J.O.R.F. of Oct. 24, 1984 and Feb. 9, 1985.

The compositions and results are given in Table I.

TABLE I

| Composition in % | Nanoparticles according to the invention | Emulsion No. 1 not according to the invention | Emulsion No. 2 not according to the invention |
| --- | --- | --- | --- |
| α-Tocopherol | 1.0 | 1.0 | 1.0 |
| Butyl cyano-acrylate | 0.2 | — | — |
| Solubilisant S 12 | — | 2.0 | — |
| Solulan 16 | — | — | 2.0 |
| Pluronic F 68 | 0.2 | — | — |
| Kathon CG | 0.1 | 0.1 | 0.1 |
| Water | qs 100 | qs 100 | qs 100 |
| Nature of the measurement | | Results | |
| SIR | 0.08 | 0.29 | 2.0 |
| EI | 2.6 at 1 H | 11.83 at 1 H | 5.67 at 1 H |
| " | 1.0 at 1 D | 1.67 at 1 D | 2.33 at 1 D |
| " | 0.0 at 2 D | 0.67 at 2 D | 1.33 at 2 D |
| " | | 0.0 at 3 D | 0.0 at 3 D |

In this Table I:

H denotes hour and D denotes day.

"Solubilisant S 12" is an emulsifier consisting of an oxyethylenated nonylphenol containing 12 moles of ethylene oxide, sold by the company "GIVAUDAN".

"Solulan 16" is an emulsifier consisting of a mixture (lanolin alcohol/oxythylenated fatty alcohols containing 16 moles of ethylene oxide) sold by the company "AMERCHOL".

"Pluronic F 68" is a surfactant consisting of a condensate of ethylene oxide and propylene oxide, sold by the company "BASF".

"Kathon CG" is a preservative consisting of a mixture of 5-chloro-2-methyl-4-isothiazolin-3-one, 2-methyl-4-isothiazolin-3-one and magnesium chloride and nitrate, sold by the company "ROHM and HAAS".

According to this table, it is seen that, to obtain the emulsions 1 and 2, 2% of emulsifier was needed in order to microdisperse 1% of α-tocopherol. On the other hand, it is seen that the composition based on nanoparticles proves distinctly less irritant to the skin than the two emulsions, and that eye irritation (EI) is also reduced, both after one hour and after two days.

EXAMPLE 2

In this further comparative example, an aqueous dispersion of nanoparticles according to the invention, having the following weight composition, was prepared according to the procedure of Example 4:

| | |
| --- | --- |
| α-Tocopherol | 5% |
| Butyl cyanoacrylate | 1% |
| Surfactant sold by the company "ICI" under the trade name "SYMPERONIC PE/F68" | 1% |
| Preservative sold by the company "ROHM and HAAS" under the trade name "KATHON CG" | 0.1% |
| Water | 92.9% |

A placebo having the following composition was also prepared:

| | |
| --- | --- |
| Oil sold by the company "DYNAMIT NOBEL" under the trade name "MIGLYOL 812" | 5% |
| Butyl cyanoacrylate | 1% |
| Surfactant sold by the company "ICI" under the trade name "SYMPERONIC PE/F68" | 1% |
| Preservative sold by the company "ROHM and HAAS" under the trade name "KATHON CG" | 0.1% |
| Water | 92.9% |

The free radical-inhibiting effect of the aqueous dispersion of nanoparticles and of the placebo was then assessed in vivo in hairless mice by subjecting them to UV radiation and measuring the content of malonodialdehyde (MDA) in the skin, since MDA formation is induced by UV radiation.

The mice are treated with a given number of applications of the test product. Each application is performed on the back of the mouse with 13.5 mg of preparation uniformly distributed over 4.5 $cm^2$, and, when there are several applications, at 24-hour intervals.

One hour after the final application, the mice are subjected to UV radiation using an apparatus of the "BIOTRONIC UV 365/312 nm" type, which emits a spectrum with absorption peaks at 365 nm (for UV-A) provided by 2 40-W tubes and at 312 nm (for UV-B) provided by a 40-W tube. The irradiations are performed at doses of 4.00 $J/cm^2$ in UV-A and 4.00 $J/cm^2$ in UV-B. Three hours after completion of the irradiation, the mice are sacrificed and the irradiated skin is cut out. After several washes, the application surface is wiped and a 100 mg fragment is introduced into 1.8 ml of phosphate buffer and then ground in an "ULTRA-TURRAX" for 1 min. The MDA is then assayed in a trichloroacetic acid medium and in the heated state by adding thiobarbituric acid, which combines with MDA to form a pink complex, and by measuring the concentration of this colored complex in a spectrophotometer.

The results are given in Table II:

TABLE II

| Test | Number of applications before irradiation | MDA content (MEAN + SEM) in nanomoles MDA/mg protein |
|---|---|---|
| Unirradiated control | 0 | 2.655 ± 0.048 |
| Irradiated control | 0 | 3.780 ± 0.277 |
| Nanoparticles | 1 | 2.651 ± 0.199 |
| " | 4 | 2.461 ± 0.255 |
| Placebo | 1 | 4.190 ± 0.323 |
| " | 4 | 3.800 ± 0.326 |

It is seen in this table that the effect of the active ingredient encapsulated in the nanoparticles is maximal from the first application onwards, and hence immediate.

EXAMPLE 3

In this third comparative example, a dispersion of nanoparticles according to the invention, having the following weight composition, was prepared according to the procedure of Example 4:

| | |
|---|---|
| Surfactant sold by the company "BASF" under the trade name "PLURONIC F 68" | 0.6% |
| Preservative sold by the company "ROHM & HAAS" under the trade name "KATHON CG" | 0.05% |
| Butyl cyanoacrylate | 0.3% |
| α-Tocopherol, radiolabelled | 1.5% |
| Water q.s. | 100% |

The radioactivity concentration of the dispersion is 120 μCi/ml.

Furthermore, a solution (not according to the invention, containing 1.5% by weight of radiolabelled α-tocopherol in silicone oil sold by the company "DOW CORNING" under the trade name "DC 200 FLUID" was prepared. The radioactivity concentration of the solution is 72 μCi/ml.

The penetration of the α-tocopherol in the dispersion of nanoparticles and in the solution in silicone oil into the different layers of the skin was then assessed. The study was performed in vitro with Franz cells, cells described in "The Journal of Investigative Dermatology, volume 64 (1975), pages 190–195".

Skin biopsies were prepared from hairless female rats weighing 230–250 g. Identical amounts of labelled α-tocopherol, in encapsulated form in nanoparticles on the one hand, and in the form of a solution in silicone oil on the other hand, were applied to the surface of these biopsies on the stratum corneum side; they were left in contact for 24 hours. The dermis was then separated mechanically from the epidermis, and the α-tocopherol:

| | |
|---|---|
| which had passed through the skin | A |
| found in the skin | |
| in the epidermis | B |
| and in the dermis | C |
| which had not penetrated into the skin | D | was assayed.

The results obtained are collated in Table III below, where they are given in percentages by weight of α-tocopherol for 100% of α-tocopherol applied.

TABLE III

| | α-tocopherol (% by weight) | | | |
|---|---|---|---|---|
| Test | A | B | C | D |
| Silicone oil | 0.73 | 25.6 | 24.3 | 54.4 |
| Nanoparticles | 0.42 | 63.8 | 17.9 | 16.7 |

In this table, it may be observed that the amount of α-tocopherol which has passed through the skin is significantly higher in the case of the solution in silicone oil than in the case of the dispersion of nanoparticles, but remains very small in both cases. Moreover, the total amount of α-tocopherol retained in the skin (epidermis and dermis) is much higher in the case of the dispersion of nanoparticles than in the case of the solution in silicone oil, the majority of the α-tocopherol remaining in the epidermis in the case of the dispersion of nanoparticles.

EXAMPLE 4

In a 1250-ml beaker, 1 g of a mixture of condensates of ethylene oxide and propylene oxide (20%/80% by weight), of average molecular weights 1750 and 8350, respectively, sold by the company "BASF" under the trade name "PLURONIC F-68), is dissolved in 500 ml of demineralized water with stirring provided by a bar magnet rotating at 400 rpm.

620 ml of absolute ethanol in which the following have been dissolved beforehand:

5 g of α-tocopherol, and 1 g of n-butyl cyanoacrylate are poured slowly dropwise into this aqueous phase.

Stirring is maintained for two hours while the temperature of the reaction medium is adjusted to 20° C. using a thermostated bath. After these two hours, the dispersion of nanoparticles obtained is transferred to a 1-liter round-bottomed flask which is placed on a rotary evaporator, and the ethanol and a part of the water are evaporated off.

95 g of a colloidal dispersion of nanoparticles are recovered containing 5 g of encapsulated α-tocopherol, the diameter and the index of polydispersity (IP) of which, measured in a "nanosizer" (Coultronics particle size analyser), are 190 nm and 1, respectively.

The index IP is assessed on a scale from 0 to 9, 0 corresponding to a very homogeneous size dispersion whereas an index of 9 indicates a high ratio of the size of the largest particles to that of the smallest.

5 g of an aqueous solution containing 0.1 g of a preservative sold by the company "ROHM & HAAS" under the trade name "KATHON CG" are finally added.

EXAMPLE 5

An aqueous dispersion having the following composition was prepared according to the same procedure as in Example 4:

| | |
|---|---|
| Condensates of ethylene oxide and propylene oxide, sold by the company "BASF" under the trade name "PLURONIC F-68" | 0.4 g |

-continued

| | |
|---|---|
| Safflower oil | 1.0 g |
| Isohexyl cyanoacrylate | 0.4 g |
| Water q.s. | 100 g |

Nanoparticles having an average diameter of 250 nm, with an index IP equal to 2, are obtained.

EXAMPLE 6

An aqueous dispersion having the following composition was prepared according to the same procedure as in Example 4:

| | |
|---|---|
| Condensates of ethylene oxide and propylene oxide, sold by the company "BASF" under the trade name "PLURONIC F-68" | 0.2 g |
| Pentaerythritol tetra(2-ethylhexanoate) | 1.0 g |
| Butyl cyanoacrylate | 0.2 g |
| Water q.s. | 100 g |

Nanoparticles having an average diameter of 250 nm, with an index IP equal to 1, are obtained.

EXAMPLE 7

An aqueous dispersion having the following composition was prepared according to the same procedure as in Example 4:

| | |
|---|---|
| Condensates of ethylene oxide and propylene oxide, sold by the company "BASF" under the trade name "PLURONIC F-68" | 0.4 g |
| Triglycerides sold by the company "DYNAMIT NOBEL" under the trade name "MIGLYOL 812" | 1.0 g |
| Vitamin A palmitate | 0.02 g |
| Butyl cyanoacrylate | 0.2 g |
| Water q.s. | 100 g |

Nanoparticles having an average diameter of 240 nm, with an index IP equal to 2, are obtained.

EXAMPLE 8

In a 200-ml beaker, 0.3 g of crosslinked polyacrylic acid, sold by the company "GOODRICH" under the trade name "CARBOPOL 940", is swollen in 41.1 g of water containing 0.1 g of methyl para-hydroxybenzoate dissolved beforehand. This operation is carried out at a temperature of 80° C.; the mixture is then gradually brought down to a temperature of 40° C. 5 g of water containing 0.1 g of natural gum sold by the company "SATIA" under the trade name "AUBY GUM X2" are added.

After homogenization, the mixture is brought down to room temperature and 10 g of aqueous solution obtained by grinding animal placental tissues, sold by the company "GATTFEFOSSE" under the trade name "PHYLDERM", and 2 g of glycerol,
1 g of hexylene glycol,
15 g of rose water
are added.

After homogenization, 0.1 g of the preservative sold by the company "DOW CHEMICAL" under the trade name "DOWICIL 200", dissolved beforehand in 5 g of water, is added. 10 g of the aqueous dispersion of nanoparticles prepared in Example 4 and 10 g of the aqueous dispersion of nanoparticles prepared according to Example 7 are added. After homogenization, 0.3 g of triethanolamine is added. A bluish-white physiological fluid having a viscosity equal to 1.6 poises and a pH equal to 7 is thereby obtained.

This physiological fluid is applied once a day to the cleansed skin of the face. After fifteen days' application, an effect of smoothing the skin of the face is observed.

EXAMPLE 9

In a 200-ml beaker, the following are dissolved in 25 g of rose water:

0.25 mg of dye "FD and C BLUE 1" marketed by the company "ALLIED CHEMICAL"; and
0.1 g of dye "D and C YELLOW 10" marketed by the company "ANSTEAD".
30.2 g of water containing 0.9 g of sodium chloride are then added, followed by 1.0 g of butylene glycol and 2.0 g of glycerol.

The mixture is homogenized and there are then added 20 g of water in which 0.05 g of crosslinked polyacrylic acid sold by the company "GOODRICH" under the trade name "CARBOPOL 1342" has been swollen.

After homogenization, 20 g of the aqueous dispersion of nanoparticles obtained in Example 6 are then added. 0.05 g of triethanolamine dissolved in 0.83 g of water is finally added. A green, very fluid moisturizing lotion having a pH equal to 6.7 is thereby obtained.

This lotion is applied twice a day after cleansing the face, especially by individuals with dry skin. After one month's application, it is observed that the skin of the face is more supple, and that the sensation of tightness caused by the dryness of the skin is attenuated.

EXAMPLE 10

380.50 g of floral water in which the following are dissolved:

0.5 g of hamamelis essence in a glycol carrier, marketed by the company "SOSHIBO",
2.5 g of hexylene glycol,
10.0 g of glycerol, and
1.0 g of condensates of ethylene oxide and propylene oxide, sold by the company "BASF" under the trade name "PLURONIC F-68" are poured into the 1-liter glass vessel of a "COS 1000" homogenizer marketed by the company "COSMETOCHEM".

This solution is homogenized by means of a scraper rotating at a speed of 30 rpm and an impeller rotating at 90 rpm, the preparation vessel being thermostated at a temperature of 20° C. During this homogenisation, an alcoholic solution composed of:

| | |
|---|---|
| ethanol | 75 g |
| butyl cyanoacrylate | 0.5 g |
| α-tocopherol acetate | 5.0 g | is added in continuous fashion in the course of 20 minutes.

After complete introduction of the alcohol phase, the speed of the impeller is reduced to 70 rpm and this stirring is maintained for two hours.

24.25 g of water containing the following preservatives in the dissolved state are then added:

| | |
|---|---|
| Preservative sold by the Company "DOW CHEMICAL" under the trade name "DOWICIL 200" | 0.5 g |
| Preservative sold by the Company "ROHM & HAAS" under the trade name "KATHON CG" | 0.25 g |

500 g of an alcoholic lotion are thereby obtained. The average diameter of the nanoparticles obtained is measured using a "BI 90" particle size analyzer (sold by the company "BROOKHAVEN"): it is 225 nm; the index of polydispersity is 2.

This lotion is applied to the body every day after a shower or bath, especially during periods of frequent exposure to sunlight. It exerts a protective action on the skin against the harmful effects of solar radiation.

EXAMPLE 11

In a 200-ml glass beaker, the following are dissolved in 24 g of liquid paraffin heated to a temperature of 65° C.:

5 g of cetyl alcohol, and 3 g of a polyethylene glycol monostearate containing 50 moles of ethylene oxide, sold by the company "ICI" under the trade name "MYRJ 53".

After the mixture has been brought down to a temperature of 50° C., an aqueous phase at the same temperature consisting of:

a solution in 44.7 g of water of 0.3 g of the mixture of preservatives sold by the company "LSN" under the trade name "ELESTAB 4112", and 20 g of the aqueous dispersion of nanoparticles obtained in Example 4 is added with stirring provided by a "MORITZ" homogeniser.

Homogenization is maintained during cooling of the product to room temperature. 100 g of a thick white cream which has a protective effect against solar radiation are thereby obtained.

This cream is applied daily to a perfectly cleansed skin; it is intended, more especially, for skins exposed daily to solar radiation.

EXAMPLE 12

In a 200-ml glass beaker, the following compounds are mixed at a temperature of 85° C. using a "MORITZ" homogeniser:

| | |
|---|---|
| Product sold by the company "CHIXEX" under the trade name "MEXANYL GO" | 5.70 g |
| Hydrogenated lanolin sold by the company "RITA" under the tradename "SUPERSAT" | 6.65 g |
| Product manufactured by the company "CHIMEX", sold under the trade name "MEXANYL GP" | 2.00 g |

After homogenisation, this first mixture is dissolved in a second mixture consisting of:

| | |
|---|---|
| Liquid purcellin oil | 3.00 g |
| Product sold by the company "CRODA" under the trade name "Liquid base CB 1145" | 3.00 g |
| Isopropyl palmitate | 4.75 g |
| Liquid paraffin | 7.9 g |

-continued

| | |
|---|---|
| White vaseline | 15 g |
| Perhydrosqualene | 0.4 g |

These two mixtures are homogenized at a temperature of 80° C. and then cooled to a temperature of 40° C. 0.8 g of perfume sold by the company "FIRMENICH" under the trade name "CHEMODERM 1008" is then added.

An aqueous phase consisting of a mixture of a solution of 0.25 g of the mixture of preservatives sold by the company "LSN" under the trade name "ELESTAB 4110", in 29.9 g of water, and 20 g of the aqueous dispersion of nano particles obtained in Example 5 is then introduced with stirring and at a temperature of 40° C.

This stirring is maintained for 20 minutes, and 0.3 g of preservative sold by the company "ROHM & HAAS" under the trade name "GERMAL 115", treated with 0.35 g of water, is then added.

After return of the mixture to room temperature, the product obtained is transferred to a triple-roller type mill.

A thick, smooth white cream is thereby obtained, intended for the care of very dry and aged skins. After a twice-daily application of this cream for 15 days, an improvement of the surface condition of the treated skin is observed.

EXAMPLE 13

An aqueous dispersion having the following composition is prepared according to the same procedure as in Example 4:

| | |
|---|---|
| Condensate of ethylene oxide and propylene oxide, sold by the company "BASF" under the trade name "Pluronic F 68" | 0.25 g |
| Bisabolol | 0.5 g |
| α-Tocopherol acetate | 0.5 g |
| Butyl cyanoacrylate | 0.2 g |
| Water q.s. | 100 g |

Nanoparticles having an average diameter of 215 nm, with an index IP equal to 1, are obtained.

EXAMPLE 14

An aqueous dispersion having the following composition was prepared according to the same procedure as in Example 4:

| | |
|---|---|
| Condensate of ethylene oxide and propylene oxide, sold by the company "BASF" under the trade name "Pluronic F 68" | 0.25 g |
| Mixture of decyl oleate, farnesol, ethyl linoleate and farnesyl acetate, sold by the company "Induchem" under the trade name "Unibiovit B 33" | 1.0 g |
| Butyl cyanoacrylate | 0.2 g |
| Water q.s. | 100 g |

Nanocapsules having an average diameter of 240 nm, with an index IP equal to 2, are obtained.

EXAMPLE 15

1) Preparation of the Dispersion of Vesicles 0.05 g of dimyristyl phosphate and 0.95 g of nonionic surfactant of formula (I):

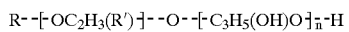 (I)

in which:

—OC₂H₃(R'),— denotes the following structures, taken mixed or separately:

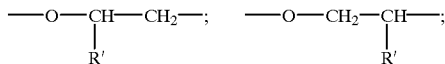

—C₃H₅(OH)O— denotes the following structures, taken mixed or separately:

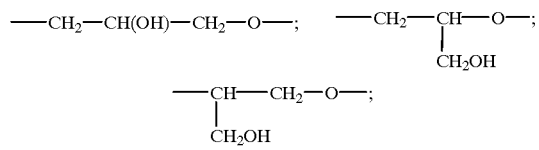

n is an average statistical value equal to 6;
R=$C_{12}H_{25}$ and R' represents an equimolar mixture of tetradecyl and hexadecyl radicals,
are weighed into a 100-ml glass beaker.

These two lipids are homogenized by heating on a hotplate to a temperature of 100° C., and the mixture is then cooled to 40° C. 27.6 g of water in which 3 g of glycerol and 0.02 g of citric acid have been dissolved beforehand are then added. The whole is homogenized by the action of a "Virtis" type ultradisperser for 2 minutes at a speed of 40,000 rpm at a temperature of 40° C. There are then added 3 g of water in which 0.1 g of preservative sold by the company "Rohm and Haas" under the trade name "Kathon CG" and 0.2 g of preservative sold by the company "Rohm and Haas" under the trade name "Germal 115" have been dissolved beforehand.

The fatty phase composed of the following mixture of products is then added:

| | |
|---|---|
| macadamia oil | 9 g |
| volatile silicone oil | 7 g |
| ethylhexyl para-methoxycinnamate sold by the company "Givaudan" under the trade name "Parsol MCX" | 0.5 g |
| 2-hydroxy-4-methoxybenzophenone sold by the company "BASF" under the trade name "Uvinul M40" | 0.5 g |
| propyl para-hydroxybenzoate | 0.05 g |

The whole is subjected to the action of a "Virtis" ultradisperser for 5 minutes at room temperature.

2) Mixing of the dispersions of Vesicles and Nanoparticles
20 g of the aqueous dispersion of nanoparticles obtained in Example 4 are then added. 35 g of water in which 0.65 g of vinylcarboxylic acid sold by the company "Goodrich" under the trade name "Carbopol 940" has been swollen are then added. After homogenization, 0.65 g of triethanolamine diluted with 1.73 g of water is finally added. A thick white cream of shiny appearance, intended for care of the face, is thereby obtained. After an application of this cream once a day for 15 days, an improvement in the surface condition of the treated skin is observed.

EXAMPLE 16

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which the following have been dissolved beforehand at a temperature of 40° C.:

125 mg of DL-polylactic acid sold by the company "Polysciences"
500 mg of α-tocopherol acetate sold by the company "Roche", and
2 mg of "Nile Red" dye (Nile Blue A Oxazone) sold by the company "Sigma", are poured slowly.

Stirring is maintained for 2 hours at a temperature of 40° C. and the mixture is then brought down to room temperature. The dispersion of nanoparticles obtained is then transferred to a 250-ml round-bottomed flask which is placed on a rotary evaporator, and the acetone is evaporated off. A fluid colloidal dispersion of nanoparticles having an average diameter of 295 nm, with an index IP equal to 2, is thereby obtained.

On microscopic examination under fluorescence conditions, a dense population of nanoparticles fluorescent to the core, with a clearly distinctive identity, homogeneous in size and agitated in Brownian movement is observed. After 2 months' storage at temperatures of +4, 25, 37 and 45° C., no modification of the appearance of the nanoparticles is observed on examination under fluorescence conditions, nor are large variations observed in their size (in all cases, the variations are less than 10% of the initial average diameter).

EXAMPLE 17

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which 125 mg of soybean lecithin, sold by the company "Lucas Meyer" under the trade name "Epikuron 170" have been dissolved beforehand at a temperature of 55° C. are poured slowly; then, after the mixture has been brought down to a temperature of 40° C., the following are dissolved:

125 mg of DL-polylactic acid sold by the company "Polysciences",
500 mg of α-tocopherol acetate sold by the company "Roche", and
2 mg of "Nile Red" dye (Nile Blue A Oxazone) sold by the company "Sigma".

Stirring is maintained for 2 hours at a temperature of 40° C. and the mixture is then brought down to room temperature. The dispersion of nanoparticles obtained is then transferred to a 250-ml round-bottomed flask which is placed on a rotary evaporator, and the acetone is evaporated off. A fluid white colloidal dispersion of nanoparticles having an average diameter of 225 nm, with an index IP equal to 2, is thereby obtained.

On microscopic examination under fluorescence conditions, a dense population of nanoparticles fluorescent to the core, with a clearly distinctive identity, homogeneous in size and agitated in Brownian movement, is observed. After 2 months' storage at temperatures of +4, 25, 37 and 45° C., no modification of the appearance of the nanoparticles is observed on examination by fluorescence microscopy, nor are large variations observed in their size (in all cases, the variations are less than 10% of the initial average diameter).

EXAMPLE 18

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which the following have been dissolved beforehand at a temperature on 40° C.

- 125 mg of DL-polylactic acid sold by the company "Polysciences", and
- 500 mg of α-tocopherol acetate sold by the company "Roche"

are poured slowly.

Stirring is maintained for 2 hours at a temperature of 40° C. and the mixture is then brought down to room temperature. The dispersion of nanoparticles obtained is then transferred to a 250-ml round-bottomed flask which is placed on a rotary evaporator, and the acetone is evaporated off. A fluid white colloidal dispersion of nanoparticles having an average diameter of 310 nm, with an index IP equal to 2, is thereby obtained.

On microscopic examination, a dense population of nanoparticles with a clearly distinctive identity, homogeneous in size and agitated in Brownian movement, is observed. After 2 months' storage at temperatures of +4, 25, 37 and 45° C., no modification of the appearance of the nanocapsules is observed, nor are large variations observed in their size (in all cases, the variations are less than 10% of the initial average diameter).

EXAMPLE 19

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which 250 mg of soybean lecithin, sold by the company "Lucas Meyer" under the trade name "Epikuron 170", have been dissolved beforehand at a temperature of 55° C. are poured slowly; then, after the mixture has been brought down to a temperature of 40° C., the following are dissolved:

- 125 mg of DL-polylactic acid sold by the company "Polysciences", and
- 500 mg of ethylhexyl para-methoxycinnamate marketed by the company "Givaudan" under the trade name "Parsol MCX".

Stirring is maintained for 2 hours at a temperature of 40° C. and the mixture is then brought down to room temperature. The dispersion of nanoparticles obtained is then transferred to a 250-ml round-bottomed flask which is placed on a rotary evaporator, and the acetone is evaporated off. A fluid white colloidal dispersion of nanoparticles having an average diameter of 240 rnm, with an index IP equal to 2, is thereby obtained.

On microscopic examination in white light, a dense population of nanoparticles with a clearly distinctive identity, homogeneous in size and agitated in Brownian movement, is observed. After 2 months' storage at temperatures of +4, 25, 37 and 45° C., no modification of the appearance of the nanoparticles is observed on microscopic examination, nor are large variations observed in their size (in all cases, the variations are less than 10% of the initial average diameter).

EXAMPLE 20

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase, 25 ml of acetone, in which 500 mg of α-tocopherol acetate and 125 mg of polymer of butyl cyanoacrylate obtained by prior self-polymerization in water of butyl cyanoacrylate monomer, isolation by centrifugation and then drying by lyophilization has been dissolved beforehand, are poured slowly. Stirring is maintained for 2 hours at room temperature. The dispersion of nanoparticles obtained is then transferred to a 250-ml round-bottomed flask which is placed on a rotary evaporator, and the acetone is evaporated off. A fluid colloidal dispersion of nanoparticles having an average diameter of 220 nm, with an index IP equal to 1, is thereby obtained.

On microscopic examination under fluorescence conditions, a dense population of nanoparticles fluorescent to the core, with a clearly distinctive identity, homogeneous in size and agitated in Brownian movement, is observed. After 2 months' storage at temperatures of +4, 25, 37 and 45° C., no modification of the appearance of the nanoparticles is observed on examination under fluorescence conditions, nor are large variations observed in their size (in all cases, the variations are less than 10% of the initial average diameter).

EXAMPLE 21

In a 100-ml beaker, 250 mg of condensate of ethylene oxide and propylene oxide (20/80%), of average molecular weights 1750 and 8350, respectively, sold by the company "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which 250 mg of soybean lecithin, sold by the company "Lucas Meyer" under the trade name "Epikuron 170", have been dissolved beforehand at a temperature of 55° C. are poured slowly; then, after the mixture has been brought down to a temperature of 40° C., the following are dissolved:

- 500 mg of α-tocopherol acetate marketed by the company "Roche", and
- 125 mg of copoly(DL-lactide/glycolide) (in the mole ratio 50:50) marketed by the company "Dupont de Nemours" under the trade name "Medisorb T.M.".

Stirring is maintained for 2 hours at a temperature of 40° C. and the mixture is then brought down to room temperature. The dispersion of nanoparticles obtained is then transferred to a 250-ml round-bottomed flask which is placed on a rotary evaporator, and the acetone is evaporated off. A fluid colloidal dispersion of nanoparticles having an average diameter of 210 nm, with an index IP equal to 1, is thereby obtained.

On microscopic examination under fluorescence conditions, a dense population of nanoparticles fluorescent to the core, with a clearly distinctive identity, homogeneous in size and agitated in Brownian movement, is observed. After 2 months' storage at temperatures of +4, 25, 37 and 45° C., no modification of the appearance of the nanoparticles is observed on examination under fluorescence conditions, nor are large variations obsreved in their size (in all cases, the variations are less than 10% of the initial average diameter).

EXAMPLE 22

In a 100 ml beaker, 250 mg of condensate of ethylene oxide and propylene oxide (20/80%), of average molecular weights 1750 and 8350, respectively, sold by the cqmpany "BASF" under the trade name "Pluronic F68", are dissolved in 50 ml of demineralized water with stirring provided by a bar magnet rotating at 400 rpm. Into this aqueous phase thermostated at a temperature of 40° C., 25 ml of acetone in which 250 mg of soybean lecithin, sold by the company "Lucas Meyer" under the trade name "Epikuron 170", have been dissolved beforehand at a temperature of 55° C. are poured slowly; then, after the mixture has been brought down to a temperature of 40° C., the following are dissolved:

500 mg of α-tocopherol acetate marketed by the company "Roche", and 125 mg of polycaprolactone marketed by the company "Aldrich".

Stirring is maintained for 2 hours at a temperature of 40° C. and the the mixture is then brought down to room temperature. The dispersion of nanoparticles obtained is then transferred to a 250-ml round-bottomed flask which is placed on a rotary evaporator, and the acetone is evaporated off. A fluid colloidal dispersion of nanoparticles having an average diameter of 195 nm, with an index IP equal to 2, is thereby obtained.

On microscopic examination in white light, a dense population of nanoparticles with a clearly distinctive identity, homogeneous in size and agitated in Brownian movement, is observed. After 2 months' storage at temperatures of +4, 25, 37 and 45° C., no modification of the appearance of the nanoparticles is observed on examination under fluorecence conditions, nor are large variations observed in their size (in all cases, the variations are less than 10% of the initial average diameter).

EXAMPLE 23

The following are weighed into a 200-ml fluted glass vessel:

2.5 g of an aqueous-alcoholic gel consisting of soybean lecithin (20%), absolute ethanol (16 degrees alcohol strength) and water, marketed by the company "Natterman" under the trade name "Natipide II", 0.01 g of ascorbyl palmitate, 5.0 g of glycerol, and 17.5 g of water.

The whole is homogenized at room temperature using a "Virtis" ultradisperser for 3 minutes at a speed of 30,000 rpm. A dispersion of liposomes having an average size of 200 nm is thereby obtained.

1 g of polyethylene glycol 400 and 3.0 g of propylene glycol are then added: the whole is mixed at room temperature for 1 minute with the "Virtis" ultradisperser. 10 g of aqueous solution obtained by grinding animal placental tissues, sold by the company "Gattefossé" under the trade name "Phylderm", are added: the whole is mixed at room temperature for 1 minute with the "Virtis" ultradisperser. 0.2 g of methyl para-hydroxybenzoate, dissolved in 30.19 g of water beforehand, is added: the whole is mixed at room temperature for 1 minute with the "Virtis" ultradisperser. 0.1 g of sodium hyaluronate swollen beforehand in 10 g of water, marketed by the company "Biotechnology", is added.

0.25 g of the mixture of vinylcarboxylic acids sold by the company "Goodrich" under the trade name "Carbopol 940", swollen beforehand in 10 g of water, is then added. The whole is mixed at room temperature for 3 minutes with the "Virtis" ultradisperser at a speed of 20,000 rpm. 0.25 g of triethanolamine is added and the mixture is homogenized for 30 seconds with the "Virtis" ultradisperser. Finally, 10 g of dispersion of nanoparticles prepared in Example 3 are added. The whole is homogenized using a "Heidolph" paddle homogenizer at a speed of 800 rpm for 30 minutes.

A beige physiological fluid is thereby obtained, which will be applied once a day to the cleansed skin of the face, before and after periods of exposure to sunlight. It is found that, despite the high frequency of exposure to sunlight and the duration of such periods of exposure, the skin shows no trace of irritation.

What is claimed is:

1. A process for the treatment of the upper layers of the epidermis comprising topically applying to the skin in an amount effective to treat the upper layers of the epidermis a composition comprising in a vehicle suitable for topical application to the skin, biodegradable polymer nanoparticles having a size ranging from 10 to 1,000 nm and encapsulating an oily phase comprising one or more of at least one active ingredient in the form of an oil or at least one active ingredient contained in an inactive carrier oil or an active oil, said active ingredient having a cosmetic action or a pharmaceutical action or both beneath the stratum corneum, said nanoparticles loaded with said active ingredient being present in an amount ranging from 0.1 to 20 percent by weight based on the total weight of said composition.

2. The process according to claim 1, wherein said biodegradable polymer constituting said nanoparticles is selected from the group consisting of a (C2–C12) alkyl cyanoacrylate, a poly-L-lactide, a poly-DL-lactide, a polyglycolide, a polycaprolactone, a polymer of 3-hydroxybutyric acid, a copoly (DL-lactide/glycolide) and a copoly (glycolide/caprolactone).

3. The process according to claim 1, wherein said polymer constituting said nanoparticles is a (C2–C6) alkyl cyanoacrylate.

4. The process according to claim 3, wherein the alkyl moiety of said cyanoacrylate is selected from the group consisting of ethyl, n-butyl, hexyl, isobutyl and isohexyl radicals.

5. The process for treatment of claim 1 wherein said active ingredient in the form of an oil or said active oil is selected from the group consisting of α-tocopherol, α-tocopherol acetate and tocopherol linoleate.

6. The process according to claim 1, wherein said active ingredient in the form of an oil or said active oil is selected from the group consisting of a triglyceride rich in linoleic acid or linolenic acid or both, pentaerythritol tetra (2-ethylhexanoate), clofibrate, fish oil, hazelnut oil, bisabolol farnesol, farnesyl acetate, ethyl linoleate and ethylhexyl paramethoxycinnamate.

7. The process according to claim 1 wherein said inactive carrier oil is selected from the group consisting of a simple triglyceride, a triglyceride modified by oxyethylenation, a volatile silicone oil and a mixture thereof.

8. The process of claim 1 wherein said active ingredient contained in an oil is selected from the group consisting of an emollient, a humectant, a free radical-inhibiting agent, an anti-inflammatory agent, a vitamin, a depigmenting agent, an anti-acne agent, an antiseborrhoeic agent, a keratolytic agent, a slimming agent and a skin coloring agent.

9. The process of claim 1 wherein the weight ratio of the biodegradable polymer of said nanoparticles to said oily phase ranges from 0.05 to 0.5.

10. The process of claim 1 wherein said composition is in the form of a physiological fluid, a lotion, an aqueous gel, an aqueous-alcoholic gel, an oil gel, a water-in-oil emulsion, an oil-in-water emulsion or an aqueous dispersion of vesicles, the constituent lipid of which is an ionic lipid or a non ionic lipid or a mixture of ionic and non ionic lipids, with or without an oily phase.

11. The process of claim 1 wherein at least a part of said nanoparticles contains at least one lipid lamella around the polymer membrane of the nanoparticle.

* * * * *